(12) United States Patent
Bowden et al.

(10) Patent No.: US 8,501,993 B2
(45) Date of Patent: Aug. 6, 2013

(54) PROCESSES FOR THE PREPARATION OF AMIDES

(75) Inventors: Martin Charles Bowden, Bracknell (GB); David Anthony Jackson, Monthey (CH); Alexandre Christian Saint-Dizier, Monthey (CH); David Drouard, Monthey (CH)

(73) Assignee: Syngenta Limited, Guildford, Surrey (GB)

( * ) Notice: Subject to any disclaimer, the term of this patent is extended or adjusted under 35 U.S.C. 154(b) by 194 days.

(21) Appl. No.: 12/992,281

(22) PCT Filed: May 11, 2009

(86) PCT No.: PCT/EP2009/055648
§ 371 (c)(1),
(2), (4) Date: Nov. 12, 2010

(87) PCT Pub. No.: WO2009/138372
PCT Pub. Date: Nov. 19, 2009

(65) Prior Publication Data
US 2011/0071315 A1 Mar. 24, 2011

(30) Foreign Application Priority Data
May 14, 2008 (GB) .................................... 0808764.5

(51) Int. Cl.
*C07C 231/02* (2006.01)
*C07C 233/05* (2006.01)

(52) U.S. Cl.
USPC ........................................... 564/139; 564/182

(58) Field of Classification Search
USPC .................................................. 564/182, 139
See application file for complete search history.

(56) References Cited

U.S. PATENT DOCUMENTS

| 6,384,278 | B1 | 5/2002 | Tang et al. |
| 6,469,005 | B1 | 10/2002 | Zeller et al. |
| 8,129,560 | B2 * | 3/2012 | Bowden et al. ............... 558/410 |

FOREIGN PATENT DOCUMENTS

| WO | 0187822 | 11/2001 |
| WO | 03/041728 | 5/2003 |
| WO | 03/042166 | 5/2003 |
| WO | WO 2007/020381 | * 2/2007 |

OTHER PUBLICATIONS

Lamberth, Clemens et al.: Synthesis and fungicidal activity of N-2-(3-methoxy-4-propargyloxy)phenethyl amides. Part 3: stretched and heterocyclic mandelamide oomyceticides; Pest Management Science, vol. 62, No. 5, 2006, pp. 446-451.
Arnold K et al: "To Catalyze or not to Catalyze? Insight into Direct Amide Bond Formation from Amines and Carboxylic Acids under Thermal and Catalyzed Conditions" Adv. Synth. Catal., vol. 348, Jan. 1, 2006, pp. 813-820.
Maki T. et al:.: "New boron(III)-catalyzed amide and ester condensation reactions" Tetrahedron, vol. 63, Mar. 31, 2007, pp. 8645-8657.
Tang P.: "Boric acid catalyzed amide formation from carboxylic acids and amines: N-benzyl-4-phenylbutyramide" Organic Synthesis, vol. 81, 2005, p. 262.

* cited by examiner

*Primary Examiner* — Shailendra Kumar
(74) *Attorney, Agent, or Firm* — R. Kody Jones

(57) ABSTRACT

The invention relates to a process for the preparation of intermediates useful in the preparation of fungicidally active phenylpropargylether derivatives. The process involves coupling of carboxylic acid with an amine in (a) the absence of a catalyst; (b) the presence of a boronic acid catalyst.

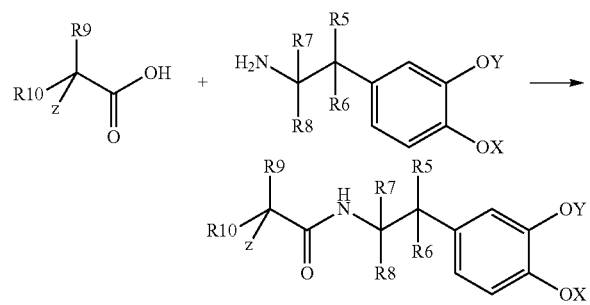

15 Claims, No Drawings

PROCESSES FOR THE PREPARATION OF AMIDES

This application is a 371 of International Application No. PCT/EP2009/055648 filed May 11, 2009, which claims priority to GB 0808764.5 filed May 14, 2008, the contents of which are incorporated herein by reference.

The present invention relates to a process for the preparation of certain fungicidally active phenylpropargylether derivatives and to processes of the preparation of certain intermediates therefore.

The fungicidally active phenylpropargylether derivatives which may be prepared according to the present invention are described, for example, in WO01/87822. These fungicidally active phenylpropargylether derivatives correspond to the formula (I)

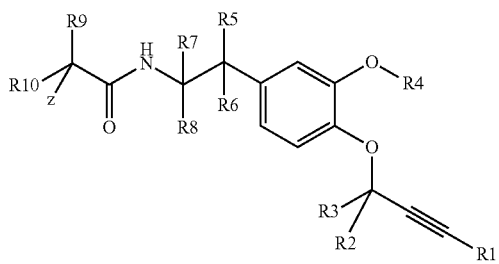

(I)

including the optical isomers thereof and mixtures of such isomers, wherein

R1 is hydrogen, alkyl, cycloalkyl or optionally substituted aryl; R2 and R3 are each independently hydrogen or alkyl; R4 is alkyl, alkenyl or alkynyl; R5, R6, R7 and R8 are each independently hydrogen or alkyl; R9 is hydrogen, optionally substituted alkyl, optionally substituted alkenyl or optionally substituted alkynyl; R10 is optionally substituted aryl or optionally substituted heteroaryl; and Z is halogen, optionally substituted aryloxy, optionally substituted alkoxy, optionally substituted alkenyloxy, optionally substituted alkynyloxy, optionally substituted arylthio, optionally substituted alkylthio, optionally substituted alkenylthio, optionally substituted alkynylthio, optionally substituted alkylsulfinyl, optionally substituted alkenylsulfinyl, optionally substituted alkynylsulfinyl, optionally substituted alkylsulfonyl, optionally substituted alkenylsulfonyl or optionally substituted alkynylsulfonyl.

A variety of methods for the preparation of the compounds of the above formula (I) have been described in WO 01/87822. WO 2007/020381 describes alternative methods for the preparation of such compounds.

It has now been surprisingly found that compounds of formula (I) may be advantageously produced by coupling the respective amine and carboxylic acid in the presence of a boronic acid catalyst or in the absence of catalyst.

In a first embodiment, the present invention relates to a process for the preparation of a compound of formula (II)

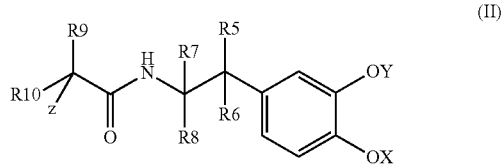

(II)

R5, R6, R7 and R8 are each independently hydrogen or alkyl; R9 is hydrogen, optionally substituted alkyl, optionally substituted alkenyl or optionally substituted alkynyl;

R10 is optionally substituted aryl or optionally substituted heteroaryl;

X is H, a protecting group, or a group of the formula (III)

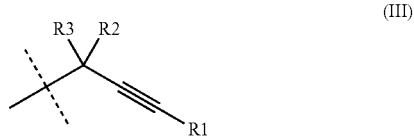

(III)

wherein

R1 is hydrogen, alkyl, cycloalkyl or optionally substituted aryl;

R2 and R3 are each independently hydrogen or alkyl;

Y is R4, H or a protecting group,

R4 is alkyl, alkenyl or alkynyl;

Z is halogen, optionally substituted aryloxy, optionally substituted alkoxy, optionally substituted alkenyloxy, optionally substituted alkynyloxy, optionally substituted arylthio, optionally substituted alkylthio, optionally substituted alkenylthio, optionally substituted alkynylthio, optionally substituted alkylsulfinyl, optionally substituted alkenylsulfinyl, optionally substituted alkynylsulfinyl, optionally substituted alkylsulfonyl, optionally substituted alkenylsulfonyl or optionally substituted alkynylsulfonyl, comprising reacting a carboxylic acid of formula (IV)

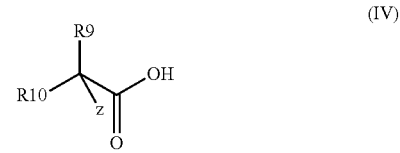

(IV)

with an amine of formula (V)

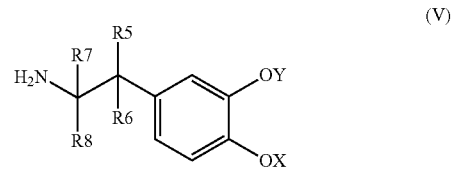

(V)

in the presence of a boronic acid catalyst.

Although use of boronic acid catalysts for synthesising amides by coupling amines with carboxylic acids is known in general, e.g. from Arnold et al., Adv. Synth. Catal. 2006, 348, 813-820, the speed and yield achieved using boronic acid catalysts with the compounds of the present invention was unexpected and surprising.

Preferably, R10 is optionally substituted aryl. More preferably, R10 is a group of the formula (VI)

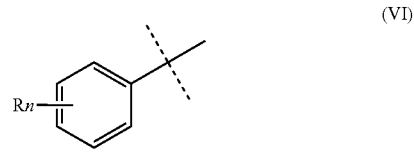

(VI)

wherein R is halogen, alkyl, alkenyl, alkynyl, cycloalkyl, cycloalkyl-alkyl, phenyl or phenylalkyl, it being possible for any of the preceding groups (other than halogen) to be substituted by one or more identical or different groups selected from: alkoxy; alkenyloxy; alkynyloxy; alkoxyalkyl; haloalkoxy; alkylthio; haloalkylthio; alkylsulfonyl; formyl; alkanoyl; hydroxy; halogen; cyano; nitro; amino; alkylamino; dialkylamino; carboxyl; alkoxycarbonyl; alkenyloxycarbonyl; and alkynyloxycarbonyl; and n is an integer from 0 to 3, preferably 0 or 1. Preferably, $R_{10}$ is halo-substituted phenyl.

For example, R is halogen, C1-C4-alkyl, C2-C4-alkenyl, C2-C4-alkynyl, C3-C6-cycloalkyl, C3-C6-cycloalkyl-C1-C4-alkyl, phenyl or phenyl-C1-C4-alkyl, it being possible for any of the preceding groups (other than halogen) to be substituted by one or more identical or different groups selected from: C1-C4-alkoxy; C2-C4-alkenyloxy; C2-C4-alkynyloxy; C1-C4-alkoxy-C1-C4-alkyl; halo-C1-C4-alkoxy; C1-C4-alkylthio; halo-C1-C4-alkylthio; C1-C4-alkysulfonyl; formyl; C1-C4-alkanoyl; hydroxy; halogen; cyano; nitro; amino; C1-C4-alkylamino; di-C1-C4-alkylamino; C2-C4-carboxyl; C1-C4-alkoxy-C2-C4-carbonyl; C2-C4-alkenyloxy-C2-C4-carbonyl; and C2-C4-alkynyloxy-C2-C4-carbonyl; and n is an integer from 0 to 3, preferably 0 or 1. Preferably, $R_{10}$ is halo-substituted phenyl.

Preferably,
R5, R6, R7 and R8 are H;
R9 is H;
R10 is a group of the formula (VI)

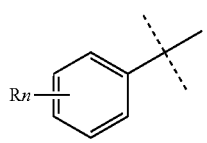

(VI)

wherein R is halogen, C1-C4-alkyl, C2-C4-alkenyl, C2-C4-alkynyl, C3-C6-cycloalkyl, C3-C6-cycloalkyl-C1-C4-alkyl, phenyl or phenyl-C1-C4-alkyl, it being possible for any of the preceding groups (other than halogen) to be substituted by one or more identical or different groups selected from: C1-C4-alkoxy; C2-C4-alkenyloxy; C2-C4-alkynyloxy; C1-C4-alkoxy-C1-C4-alkyl; halo-C1-C4-alkoxy; C1-C4-alkylthio; halo-C1-C4-alkylthio; C1-C4-alkysulfonyl; formyl; C1-C4-alkanoyl; hydroxy; halogen; cyano; nitro; amino; C1-C4-alkylamino; di-C1-C4-alkylamino; C2-C4-carboxyl; C1-C4-alkoxy-C2-C4-carbonyl; C2-C4-alkenyloxy-C2-C4-carbonyl; and C2-C4-alkynyloxy-C2-C4-carbonyl; and n is an integer from 0 to 3, preferably 0 or 1; $R_{10}$ is preferably halosubstituted phenyl;
z is C3-C4 alkynyloxy;
Y is R4; R4 is $CH_3$;
X is H, a protecting group, or a group of the formula (III)

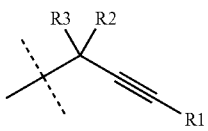

(III)

wherein R1, R2, and R3 are hydrogen.

In a further aspect, the invention provides a process for the preparation of a compound of formula (II)

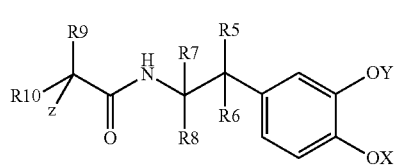

(II)

wherein
R5, R6, R7 and R8 are H;
R9 is H;

R10 is a group of the formula (VI)

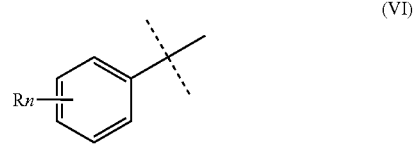

(VI)

wherein R is halogen, C1-C4-alkyl, C2-C4-alkenyl, C2-C4-alkynyl, C3-C6-cycloalkyl, C3-C6-cycloalkyl-C1-C4-alkyl, phenyl or phenyl-C1-C4-alkyl, it being possible for any of the preceding groups (other than halogen) to be substituted by one or more identical or different groups selected from: C1-C4-alkoxy; C2-C4-alkenyloxy; C2-C4-alkynyloxy; C1-C4-alkoxy-C1-C4-alkyl; halo-C1-C4-alkoxy; C1-C4-alkylthio; halo-C1-C4-alkylthio; C1-C4-alkysulfonyl; formyl; C1-C4-alkanoyl; hydroxy; halogen; cyano; nitro; amino; C1-C4-alkylamino; di-C1-C4-alkylamino; C2-C4-carboxyl; C1-C4-alkoxy-C2-C4-carbonyl; C2-C4-alkenyloxy-C2-C4-carbonyl; and C2-C4-alkynyloxy-C2-C4-carbonyl; and n is an integer from 0 to 3, preferably 0 or 1; R10 is preferably halosubstituted phenyl;
z is C3-C4 alkynyloxy;
Y is $R_4$; $R_4$ is $CH_3$;
X is H, a protecting group, or a group of the formula (III)

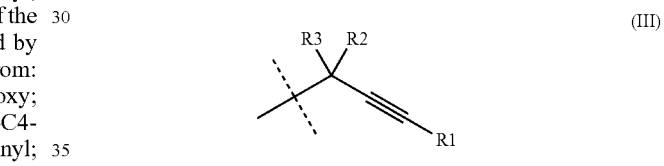

(III)

wherein R1, R2, and R3 are hydrogen;
comprising reacting a carboxylic acid of formula (IV)

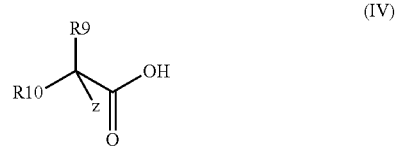

(IV)

with an amine of formula (V)

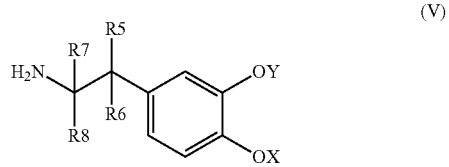

(V)

wherein the reaction is conducted in the absence of a catalyst.

It has been surprisingly found that this reaction proceeds with commercially useful yields even in the absence of catalyst. This is contrary to teaching in standard organic chemistry texts such as Advanced Organic Chemistry, Jerry March $4^{th}$ edition [ISBN 0-471-60180-2], which indicates on page 419 that procedures to obtain amides involving treatment of carboxylic acids with ammonia are seldom of preparative value.

More preferably (in any aspect of the invention), R10 is halophenyl. More preferably, R10 is 4-halophenyl. Most preferably, R10 is 4-chlorophenyl.

Preferably, R9 is hydrogen.

Preferably, Z is optionally substituted alkynyloxy. More preferably, Z is O-propargyl (—CH$_2$CCH).

Preferably, R5 is hydrogen. Preferably, R6 is hydrogen. Preferably, R7 is hydrogen. Preferably, R8 is hydrogen.

Preferably, R5, R6, R7, R8 are all hydrogen.

Preferably, X is H.

Preferably, Y is R4;

Preferably, R4 is alkyl, more preferably CH$_3$;

In a further embodiment, the invention relates to a compound obtainable by the process of the invention. In a further embodiment, the invention relates to a compound obtained by the process of the invention. In a still further embodiment, the invention relates to a process substantially as described herein with reference to the Examples.

Further Transformations

The invention provides compounds (including novel compounds) which may be useful as intermediates in the preparation of fungicidally active phenylpropargylether derivatives.

In certain embodiments, the processes of the invention give rise directly to the fungicidally active phenylpropargylether derivatives as defined in WO01/87822 without the need for further transformation, e.g.:

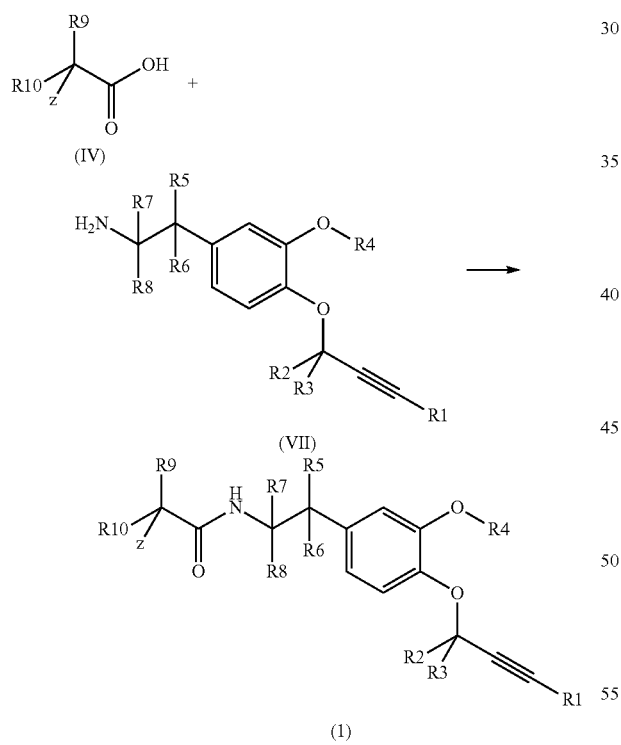

wherein R1 to R10 and Z are as defined above.

In alternative embodiments, further chemical transformation of the intermediate of formula (II) to obtain fungicidally active phenylpropargylether derivatives of the formula (I) above may be necessary.

For example, in embodiments wherein Y represents a protecting group, this may be removed under appropriate conditions, and the phenol (VIII) alkylated with a suitable alkylating agent LG-R4 (wherein LG represents a leaving group).

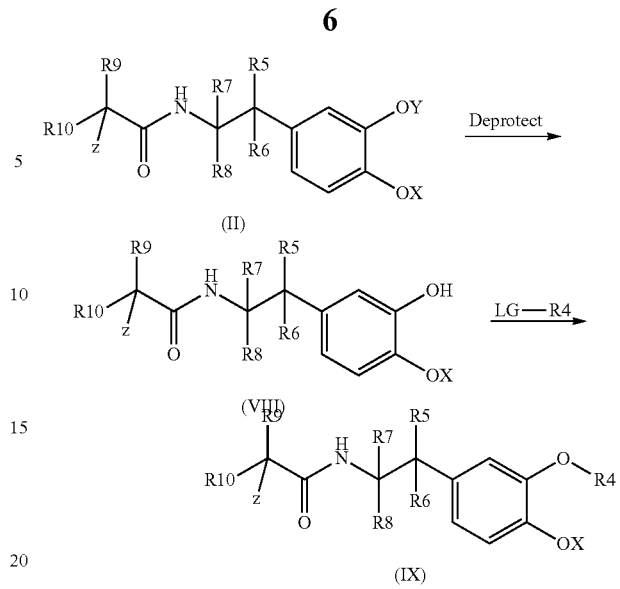

Suitable conditions for the removal of the protecting group Y will depend on the nature of this group, and will be apparent to the skilled person.

In a preferred embodiment, Y is R4, and X is hydrogen. In this embodiment, alkylation of phenol (XI) is achieved with compound (XII), wherein LG represents a leaving group and R1, R2 and R3 are as defined above to give a final compound of formula (I). Suitable reagents and conditions for such a transformation are described in WO 01/087822

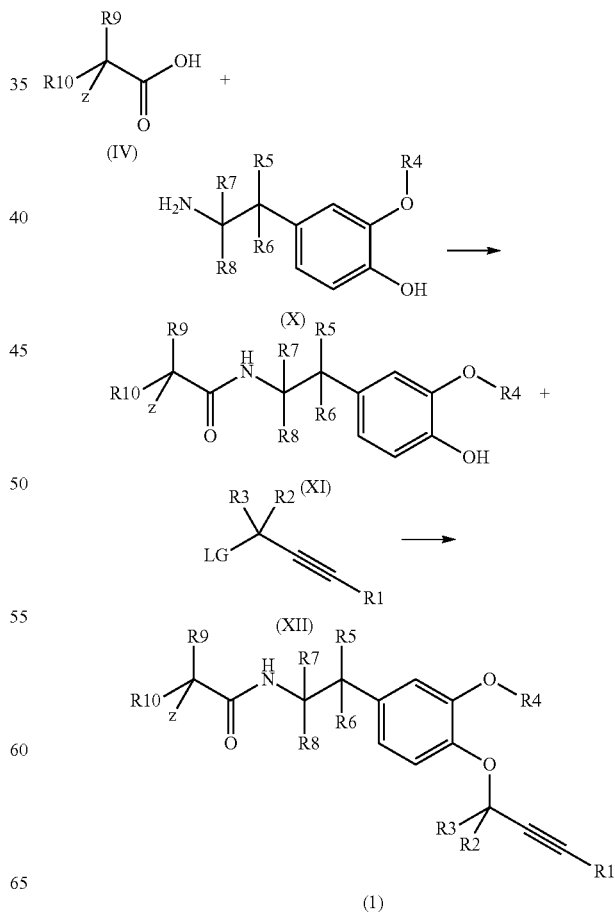

In a very highly preferred embodiment, the invention relates to a process for the preparation of 2-(4-Chloro-phenyl)-N-[2-(4-hydroxy-3-methoxy-phenyl)-ethyl]-2-prop-2-ynyloxy-acetamide (XIII)

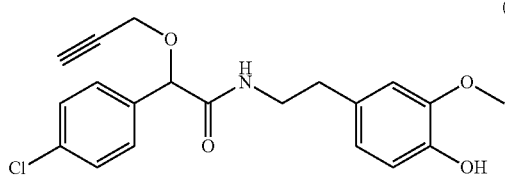

(XIII)

comprising reacting 2-(4-Chloro-phenyl)-prop-2-ynyloxy-acetic acid (XIV)

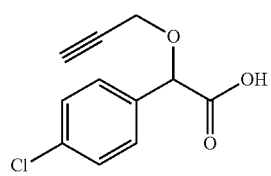

(XIV)

with 4-(2-aminoethyl)-2-methoxy phenol (XV)

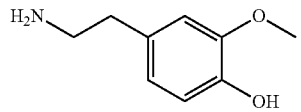

(XV)

(a) in the absence of a catalyst;
(b) in the presence of a boronic acid catalyst.

Optionally and preferably, the compound of formula (XIII) is converted to mandipropamid (2-(4-Chloro-phenyl)-N-[2-(3-methoxy-4-prop-2-ynyl-phenyl)-ethyl]-2-prop-2-ynyloxyacetamide (XVI)) by reaction with a compound of formula (XVII), wherein LG is a leaving group, preferably bromide.

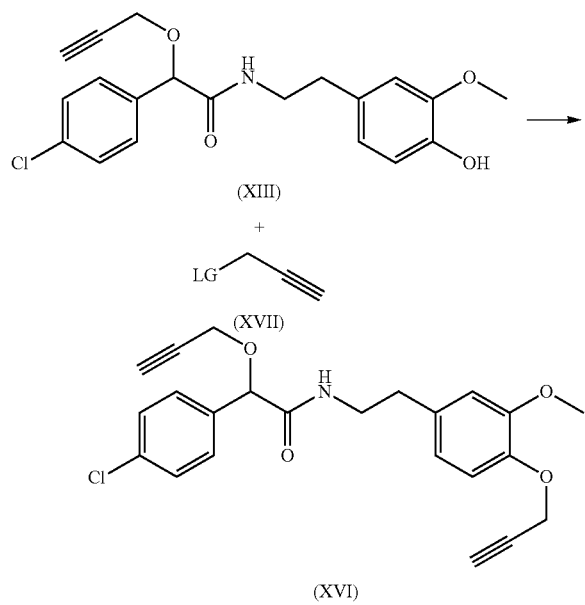

Appropriate conditions for this transformation are disclosed in e.g. WO 2007/020381.

In a further embodiment the invention relates to a process for the preparation of Mandipropamid (2-(4-Chloro-phenyl)-N-[2-(3-methoxy-4-prop-2-ynyl-phenyl)-ethyl]-2-prop-2-ynyloxyacetamide (XVI))

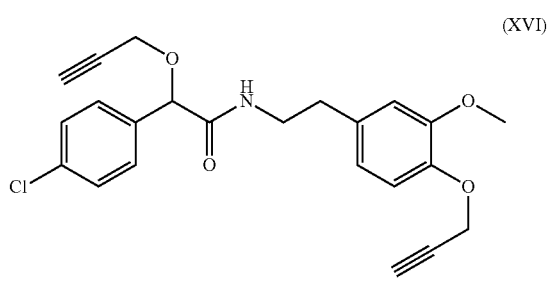 [SMILES: C#CCOc1ccc(CCNC(=O)C(OCC#C)c2ccc(Cl)cc2)cc1OC]

(XVI)

comprising reacting 2-(4-Chloro-phenyl)-prop-2-ynyloxy-acetic acid (XIV)

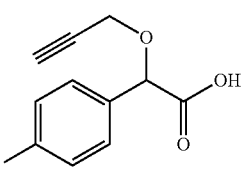

(XIV)

with compound (XVIII)

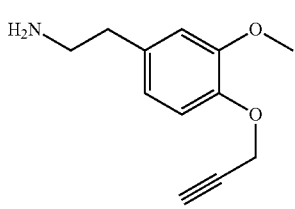

(XVIII)

(a) in the absence of a catalyst;
(b) in the presence of a boronic acid catalyst.

Solvent

The reaction of the invention is optionally (and preferably) conducted in a suitable solvent. Suitable solvents include, but are not limited to, linear, branched or cyclic aliphatic hydrocarbons, such as ligroin or cyclohexane, pentane, hexane, heptane, octane, as well as aromatic solvents, such as benzene, toluene, xylene, monochlorobenzene, dichlorobenzene, trichlorobenzene.

Preferred solvents are xylene, monochlorobenzene and toluene. A particularly preferred solvent is xylene.

Temperature

The reaction of the invention may be carried out at a temperature such that an acceptable rate of reaction is attained. Preferably, the reaction is conducted at a temperature of from 0° C. to 200° C. More preferably, the reaction is conducted at a temperature of from 50° C. to 180° C. More preferably, the reaction is conducted at a temperature of from 100° C. to 170° C. More preferably, the reaction is conducted at a temperature of from 140° C. to 160° C.

Removal of Water

Preferably, provision is made for removal of water from the reaction mixture, e.g. removal of water prior to completion of the reaction. Water may be removed from the reaction continuously. A suitable method is azeotropic removal of water. Suitable apparatus for conducting azeotropic removal of water will be known to those skilled in the art. We have found that removal of water is highly desirable in order to achieve a commercially useful conversion to product.

Boronic Acid

Examples of the boronic acid include boric acid, phenylboronic acid, 2-methylphenylboronic acid, 3-methylphenylboronic acid, 4-methylphenylboronic acid, 2,3-dimethylphenylboronic acid, 4-dimethylphenylboronic acid, 2,5-dimethylphenylboronic acid, 2-ethylphenylboronic acid, 4-n-propylphenylboronic acid, 4-isopropylphenylboronic acid, 4-n-butylphenylboronic acid, 4-tert-butylphenylboronic acid, 1-naphthylboronic acid, 2-naphthylboronic acid, 2-biphenylboronic acid, 3-biphenylboronic acid, 4-biphenylboronic acid, 2-fluoro-4-biphenylboronic acid, 2-fluorenylboronic acid, 9-fluorenylboronic acid, 9-phenanthrenylboronic acid, 9-anthracenylboronic acid, 1-pyrenylboronic acid, 2-trifluoromethylphenylboronic acid, 3-trifluoromethylphenylboronic acid, 4-trifluorophenylboronic acid, 3,5-bis(trifluoromethyl)phenylboronic acid, 2-methoxyphenylboronic acid, 3-methoxyphenylboronic acid, 4-methoxyphenylboronic acid, 2,5-dimethoxyphenylboronic acid, 4,5-dimethoxyphenylboronic acid, 2,4-dimethoxyphenylboronic acid, 2-ethoxyphenylboronic acid, 3-ethoxyphenylboronic acid, 4-ethoxyphenylboronic acid, 4-phenoxyboronic acid, 4-methylenedioxyphenylboronic acid, 2-fluorophenylboronic acid, 3-fluorophenylboronic acid, 4-fluorophenylboronic acid, 2,4-difluorophenylboronic acid, 2,5-difluorophenylboronic acid, 4,5-difluorophenylboronic acid, 3,5-difluorophenylboronic acid, 2-formylphenylboronic acid, 3-formylphenylboronic acid, 4-formylphenylboronic acid, 3-formyl-4-methoxyphenylboronic acid, 2-cyanophenylboronic acid, 3-cyanophenylboronic acid, 4-cyanophenylboronic acid, 3-nitrophenylboronic acid, 3-acetylphenylboronic acid, 4-acetylphenylboronic acid, 3-trifluoroacetylphenylboronic acid, 4-trifluoroacetylphenylboronic acid, 4-methylthiophenylboronic acid, 4-vinylphenylboronic acid, 3-carboxyphenylboronic acid, 4-carboxyphenylboronic acid, 3-aminophenylboronic acid, 2-(N,N-dimethylamino)phenylboronic acid, 3-(N,N-dimethylamino)phenylboronic acid, 4-(N,N-dimethylamino)phenylboronic acid, 2-(N,N-diethylamino)phenylboronic acid, 3-(N,N-diethylamino)phenylboronic acid, 4-(N,N-diethylamino)phenylboronic acid, 2-(N,N-dimethylaminomethyl)phenylboronic acid, furan-2-boronic acid, furan-3-boronic acid, 4-formyl-2-furanboronic acid, dibenzofuran-4-boronic acid, benzofuran-2-boronic acid, thiophene-2-boronic acid, thiophene-3-boronic acid, 5-methylthiophene-2-boronic acid, 5-chlorothiophene-2-boronic acid, 4-methylthiophene-2-boronic acid, 5-methylthiophene-2-boronic acid, 2-acetylthiophene-5-boronic acid, 5-methylthiophene-2-boronic acid, benzothiophene-2-boronic acid, dibenzothiophene-4-boronic acid, pyridine-3-boronic acid, pyridine-4-boronic acid, pyrimidine-5-boronic acid, quinoline-8-boronic acid, isoquinoline-4-boronic acid, 4-benzenebis(boronic acid), phenylboronic acid-pinacol ester, and 4-cyanophenylboronic acid-pinacol ester.

Preferred boronic acids for use as a catalyst in the invention are aryl boronic acids and boric acid, particularly aryl boronic acids. Most preferred are 2-(N,N-dimethylaminomethyl)phenylboronic acid and phenyl boronic acid.

Starting Materials

Carboxylic acids (IV) and amines (V) are suitably prepared using methods taught, for example, in WO 01087822 and WO 2007020381.

Amount of Catalyst

Preferably, the amount of catalyst employed is up to 50 mol % based on the amount of carboxylic acid (IV). More preferably, the amount of catalyst employed is up to 25 mol % based on the amount of carboxylic acid (IV). More preferably, the amount of catalyst employed is up to 15 mol % based on the amount of carboxylic acid (IV).

Preferably, the amount of catalyst employed is at least 0.01 mol % based on the amount of carboxylic acid (IV). More preferably, the amount of catalyst employed is at least 0.1 mol % based on the amount of carboxylic acid (IV). More preferably, the amount of catalyst employed is at least 1 mol % based on the amount of carboxylic acid (IV).

Preferably, the amount of catalyst employed is between 0.01 and 50 mol % based on the amount of carboxylic acid (IV). More preferably, the amount of catalyst employed is between 0.1 and 25 mol % based on the amount of carboxylic acid (IV). More preferably, the amount of catalyst employed is between 1 and 15 mol % based on the amount of carboxylic acid (IV). More preferably, the amount of catalyst employed is between 8 and 12 mol % based on the amount of carboxylic acid (IV).

Preferably, the amount of catalyst employed is up to 50 mol % based on the amount of amine (V). More preferably, the amount of catalyst employed is up to 25 mol % based on the amount of amine (V). More preferably, the amount of catalyst employed is up to 15 mol % based on the amount of amine (V).

Preferably, the amount of catalyst employed is at least 0.01 mol % based on the amount of amine (V). More preferably, the amount of catalyst employed is at least 0.1 mol % based on the amount of amine (V). More preferably, the amount of catalyst employed is at least 1 mol % based on the amount of amine (V).

Preferably, the amount of catalyst employed is between 0.01 and 50 mol % based on the amount of amine (V). More preferably, the amount of catalyst employed is between 0.1 and 25 mol % based on the amount of amine (V). More preferably, the amount of catalyst employed is between 1 and 15 mol % based on the amount of amine (V). More preferably, the amount of catalyst employed is between 8 and 12 mol % based on the amount of amine (V).

Usually one type of catalyst will be used in a reaction. However, the invention also covers reactions in which more than one type of catalyst is used, e.g. either separately, sequentially or simultaneously.

Leaving Group

As used herein, the term "leaving group" refers to a group that can be displaced by a nucleophile (e.g. a hydroxyl group) to form a chemical bond (in the case of a hydroxyl group as nucleophile, an ether).

Examples of leaving groups are chloro, bromo, iodo, and alkyl- and aryl sulphonates (e.g. tosylate, mesylate, trifluomethanesulphonate).

Protecting Group

Suitable protecting groups, along with conditions for their introduction and removal, are well known to those skilled in the art, and are for example taught in *Greene's Protective Groups in Organic Synthesis* (Wiley-Interscience; 4 edition (Oct. 30, 2006)).

Examples of suitable hydroxyl-protecting groups are ethers (e.g. benzyl ethers) and silyl ethers (e.g. trimethylsilyl ether, t-butyldimethylsilyl ether).

EXAMPLES

Example 1

Preparation of 2-(4-Chloro-phenyl)-N-[2-(4-hydroxy-3-methoxy-phenyl)-ethyl]-2-prop-2-ynyloxy-acetamide—Catalyst free

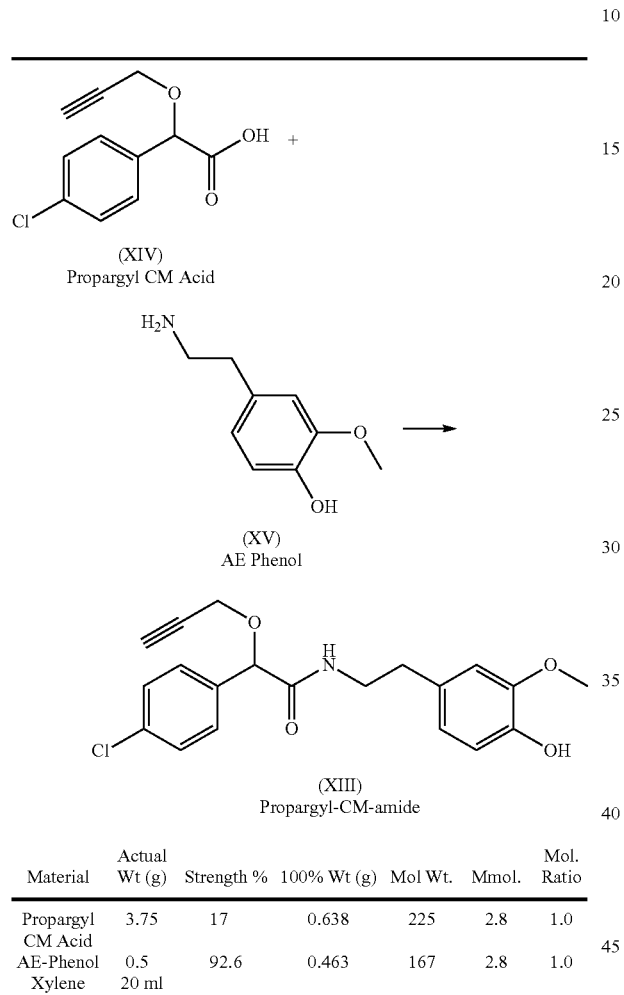

| Material | Actual Wt (g) | Strength % | 100% Wt (g) | Mol Wt. | Mmol. | Mol. Ratio |
|---|---|---|---|---|---|---|
| Propargyl CM Acid | 3.75 | 17 | 0.638 | 225 | 2.8 | 1.0 |
| AE-Phenol | 0.5 | 92.6 | 0.463 | 167 | 2.8 | 1.0 |
| Xylene | 20 ml | | | | | |

Procedure

A 50 ml three neck round bottom flask was fitted with a thermometer, magnetic stirrer and Dean and Stark apparatus filled with 3 Å molecular sieves (8-12 mesh) and 5 ml of xylene. The system was purged with nitrogen.

AE-phenol (0.5 g), propargyl-CM-acid (3.75 g) and xylene (20 ml) were charged to the flask. The resulting white slurry was heated to reflux (~143° C.), and held at this temperature for 4 hours. The initial slurry became a yellow-brown solution as the reaction progressed.

The reaction was monitored by HPLC, 100% conversion being achieved after 4 h.

The reaction mass was cooled to ambient temperature, and then acetonitrile (20 ml) was added. Concentration of the mixture in vacuo gave the desired product in 83% yield and good quality.

Product identity was confirmed by NMR, HPLC, GCMS, and IR comparison with authentic material.

Example 2

Preparation of 2-(4-Chloro-phenyl)-N-[2-(4-hydroxy-3-methoxy-phenyl)-ethyl]-2-prop-2-ynyloxy-acetamide—Catalysed

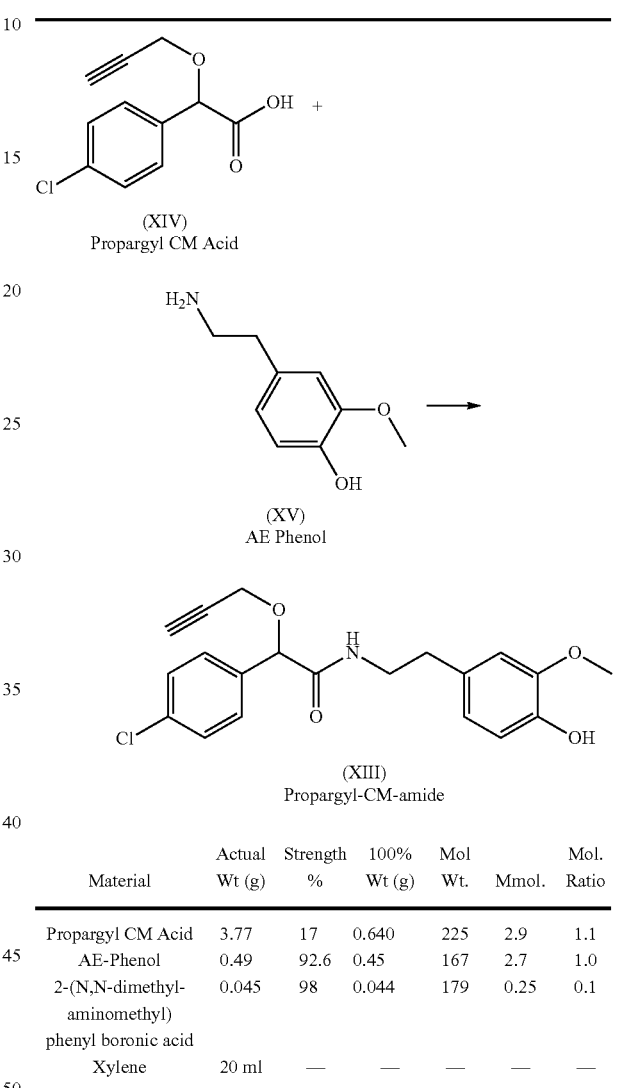

| Material | Actual Wt (g) | Strength % | 100% Wt (g) | Mol Wt. | Mmol. | Mol. Ratio |
|---|---|---|---|---|---|---|
| Propargyl CM Acid | 3.77 | 17 | 0.640 | 225 | 2.9 | 1.1 |
| AE-Phenol | 0.49 | 92.6 | 0.45 | 167 | 2.7 | 1.0 |
| 2-(N,N-dimethylaminomethyl)phenyl boronic acid | 0.045 | 98 | 0.044 | 179 | 0.25 | 0.1 |
| Xylene | 20 ml | — | — | — | — | — |

Procedure

A 50 ml three neck round bottom flask was fitted with a thermometer, magnetic stirrer and Dean and Stark apparatus filled with 3 Å molecular sieves (8-12 mesh) and 5 ml of xylene. The system was purged with nitrogen.

AE-phenol (0.49 g), propargyl-CM-acid (3.77 g), 2-(N,N-dimethylaminomethyl)phenyl boronic acid (0.045 g) and xylene (20 ml) were charged to the flask. The resulting white slurry was heated to reflux (~143° C.), and held at this temperature for 2 hours.

The reaction was monitored by HPLC, 96% conversion being achieved after 1 h and 100% conversion after 2 h.

Product identity was confirmed by NMR, HPLC, GCMS, and IR comparison with authentic material.

Example 3

Preparation of 2-(4-Chloro-phenyl)-N-[2-(4-hydroxy-3-methoxy-phenyl)-ethyl]-2-prop-2-ynyloxy-acetamide—Catalysed

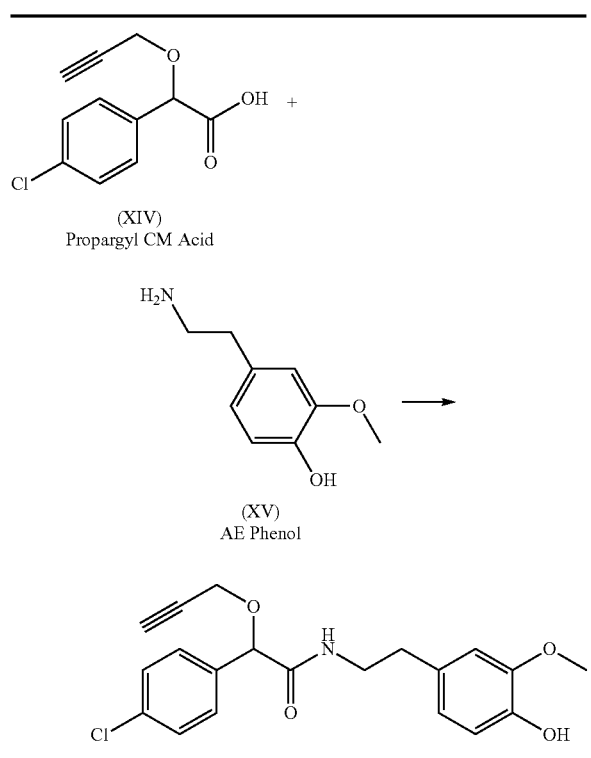

(XIV) Propargyl CM Acid (XV) AE Phenol (XIII) Propargyl-CM-amide

| Material | Actual Wt (g) | Strength % | 100% Wt (g) | Mol Wt. | Mmol. | Mol. Ratio |
|---|---|---|---|---|---|---|
| Propargyl CM Acid | 201.44 | 33.7 | 67.89 | 225 | 302 | 1.0 |
| AE-Phenol | 57.62 | 93.3 | 53.76 | 167 | 321 | 1.06 |
| Phenyl boronic acid | 3.78 | 97 | 3.67 | 122 | 30.1 | 0.1 |
| Monochlorobenzene | 536 ml | — | — | — | — | — |

Procedure

A 0.5 l three glass reactor was fitted with a thermometer, 3-blades agitator and Dean and Stark apparatus. The system was purged with nitrogen.

AE-phenol (57.62 g), propargyl-CM-acid (201.44 g), phenyl boronic acid (3.78 g) and monochlorobenzene (536 ml) were charged to the reactor. The resulting white slurry was heated to reflux (~132° C.), and held at this temperature for 6 hours.

The reaction was monitored by HPLC, 32% conversion being achieved after 6 h.

Product identity was confirmed by HPLC and comparison with authentic material.

Example 4

Preparation of 2-(4-Chloro-phenyl)-N-[2-(4-hydroxy-3-methoxy-phenyl)-ethyl]-2-prop-2-ynyloxy-acetamide—Catalysed

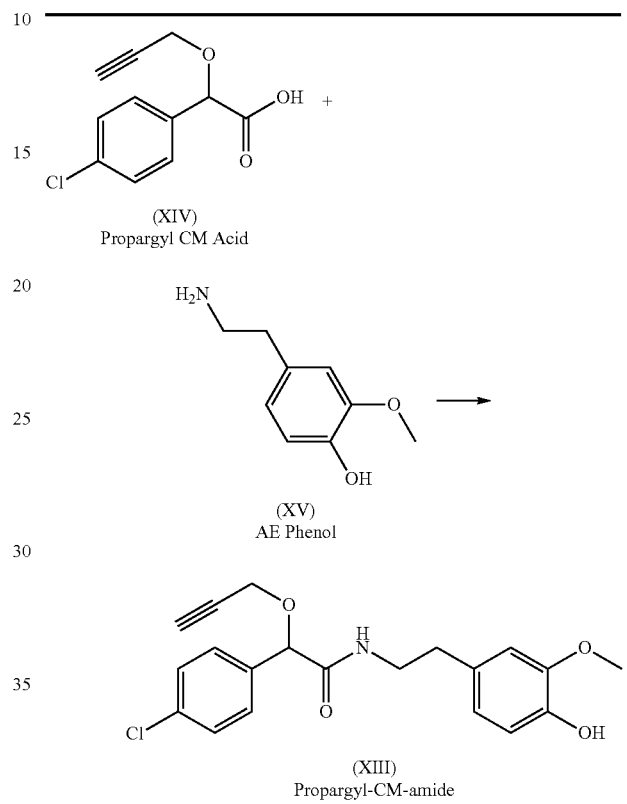

(XIV) Propargyl CM Acid (XV) AE Phenol (XIII) Propargyl-CM-amide

| Material | Actual Wt (g) | Strength % | 100% Wt (g) | Mol Wt. | Mmol. | Mol. Ratio |
|---|---|---|---|---|---|---|
| Propargyl CM Acid | 147.93 | 33.7 | 49.85 | 225 | 221 | 1.0 |
| AE-Phenol | 42.1 | 93.3 | 39.28 | 167 | 234 | 1.06 |
| Phenyl boronic acid | 2.73 | 97 | 2.65 | 122 | 21.7 | 0.1 |
| Xylene | 358 ml | — | — | — | — | — |

Procedure

A 0.5 l three glass reactor was fitted with a thermometer, 3-blades agitator and Dean and Stark apparatus. The system was purged with nitrogen.

Propargyl-CM-acid (147.93 g) as a solution in monochlorobenzene was charged to the reactor. After vacuum distillation of monochlorobenzene, AE-phenol (42.1 g), phenyl boronic acid (2.73 g) and xylene (358 ml) were charged to the flask. The resulting white slurry was heated to reflux (~143° C.), and held at this temperature for 6 hours.

The reaction was monitored by HPLC, 85% conversion being achieved after 5 h and 87% conversion after 6 h.

Product identity was confirmed by HPLC and comparison with authentic material.

Example 5

Preparation of 2-(4-Chloro-phenyl)-N-[2-(4-hydroxy-3-methoxy-phenyl)-ethyl]-2-prop-2-ynyloxy-acetamide—Catalysed

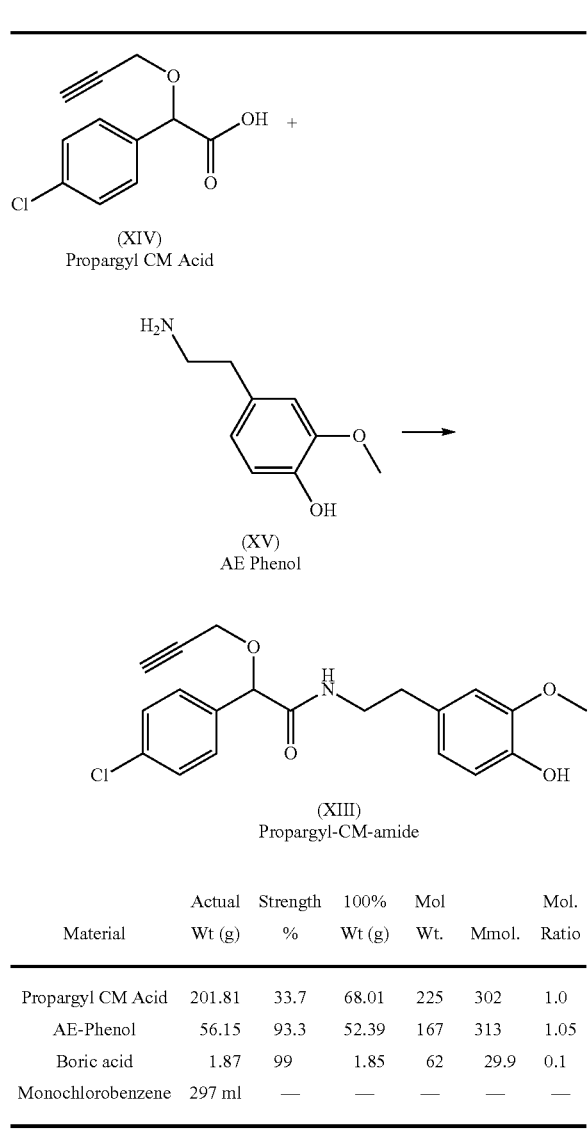

(XIV) Propargyl CM Acid (XV) AE Phenol (XIII) Propargyl-CM-amide

| Material | Actual Wt (g) | Strength % | 100% Wt (g) | Mol Wt. | Mmol. | Mol. Ratio |
|---|---|---|---|---|---|---|
| Propargyl CM Acid | 201.81 | 33.7 | 68.01 | 225 | 302 | 1.0 |
| AE-Phenol | 56.15 | 93.3 | 52.39 | 167 | 313 | 1.05 |
| Boric acid | 1.87 | 99 | 1.85 | 62 | 29.9 | 0.1 |
| Monochlorobenzene | 297 ml | — | — | — | — | — |

Procedure

A 0.5 l three glass reactor was fitted with a thermometer, 3-blades agitator and Dean and Stark apparatus. The system was purged with nitrogen.

AE-phenol (56.15 g), propargyl-CM-acid (201.81 g), boric acid (1.87 g) and monochlorobenzene (297 ml) were charged to the reactor. The resulting white slurry was heated to reflux (~132° C.), and held at this temperature for 6 hours.

The reaction was monitored by HPLC, 9% conversion being achieved after 6 h. Product identity was confirmed by HPLC and comparison with authentic material.

Example 6

Preparation of 2-(4-Chloro-phenyl)-N-[2-(4-hydroxy-3-methoxy-phenyl)-ethyl]-2-prop-2-ynyloxy-acetamide—Catalysed

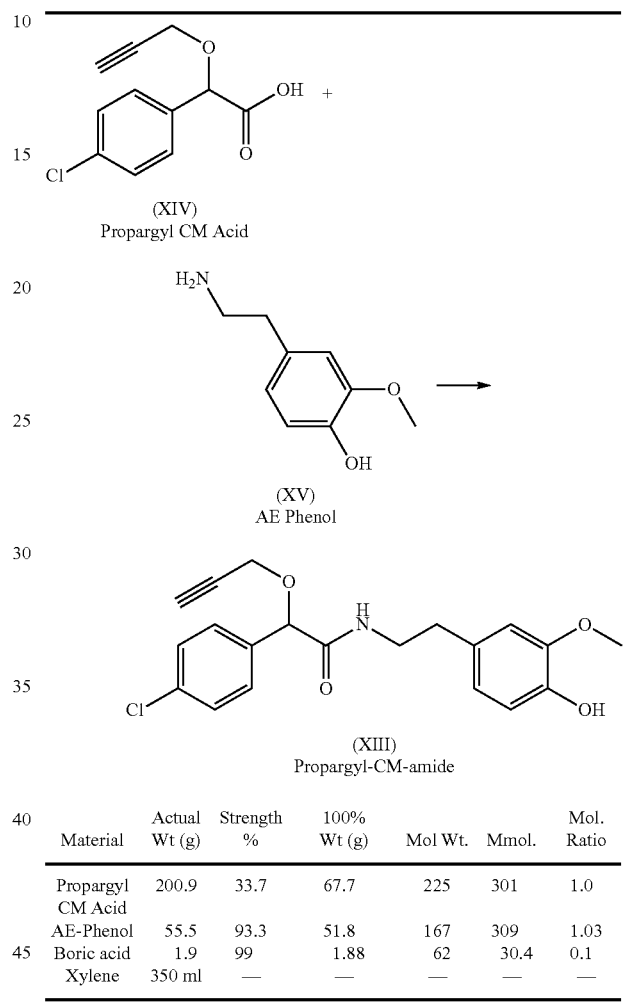

(XIV) Propargyl CM Acid (XV) AE Phenol (XIII) Propargyl-CM-amide

| Material | Actual Wt (g) | Strength % | 100% Wt (g) | Mol Wt. | Mmol. | Mol. Ratio |
|---|---|---|---|---|---|---|
| Propargyl CM Acid | 200.9 | 33.7 | 67.7 | 225 | 301 | 1.0 |
| AE-Phenol | 55.5 | 93.3 | 51.8 | 167 | 309 | 1.03 |
| Boric acid | 1.9 | 99 | 1.88 | 62 | 30.4 | 0.1 |
| Xylene | 350 ml | — | — | — | — | — |

Procedure

A 0.5 l three glass reactor was fitted with a thermometer, 3-blades agitator and Dean and Stark apparatus. The system was purged with nitrogen.

Propargyl-CM-acid (200.9 g) as a solution in monochlorobenzene was charged to the reactor. After vacuum distillation of monochlorobenzene, AE-phenol (55.5 g), boric acid (1.9 g) and xylene (350 ml) were charged to the flask. The resulting white slurry was heated to reflux (~143° C.), and held at this temperature for 6 hours.

The reaction was monitored by HPLC, 14% conversion being achieved after 6 h.

Product identity was confirmed by HPLC and comparison with authentic material.

It is believed that the lower yield of product obtained in Examples 3-6 was due to use of a reactor that was not optimised for this type of reaction.

The invention claimed is:
1. A process for the preparation of a compound of formula (II)

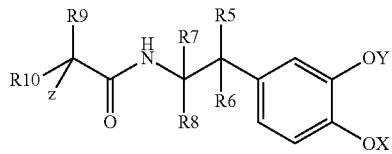

R5, R6, R7 and R8 are each independently hydrogen or alkyl;
R9 is hydrogen, optionally substituted alkyl, optionally substituted alkenyl or optionally substituted alkynyl;
R10 is optionally substituted aryl, optionally substituted heteroaryl;
X is H, a protecting group, or a group of the formula (III)

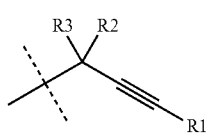

wherein
R1 is hydrogen, alkyl, cycloalkyl or optionally substituted aryl;
R2 and R3 are each independently hydrogen or alkyl;
Y is R4, H or a protecting group;
R4 is alkyl, alkenyl or alkynyl;
z is optionally substituted alkynyloxy;
comprising reacting a carboxylic acid of formula (IV)

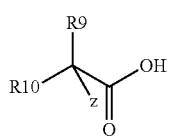

with an amine of formula (V)

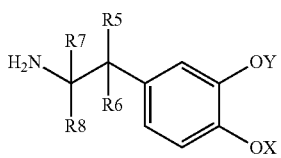

wherein the reaction is conducted in the presence of an arylboronic acid catalyst or boric acid.
2. The process according to claim 1, wherein the reaction is conducted in the presence of an aryl boronic acid catalyst.
3. The process according to claim 1, wherein the catalyst is 2-(N,N-dimethylaminomethyl)phenyl boronic acid, phenyl boronic acid or boric acid.
4. The process according to claim 1 wherein R10 is 4-chlorophenyl.
5. The process according to claim 1 wherein R9 is hydrogen.
6. The process according to claim 1 wherein z is O-propargyl.
7. The process according to claim 1 wherein R5 to R8 are hydrogen.

8. The process according to claim 1 wherein Y is methyl.
9. The process according to claim 1 wherein X is H.
10. The process according to claim 1, wherein
R5, R6, R7 and R8 are H;
R9 is H;
R10 is a group of the formula (VI)

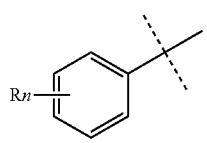

wherein R is halogen, C1-C4-alkyl, C2-C4-alkenyl, C2-C4-alkynyl, C3-C6-cycloalkyl, C3-C6-cycloalkyl-C1-C4-alkyl, phenyl or phenyl-C1-C4-alkyl, it being possible for any of the preceding groups (other than halogen) to be substituted by one or more identical or different groups selected from: C1-C4-alkoxy; C2-C4-alkenyloxy; C2-C4-alkynyloxy; C1-C4-alkoxy-C1-C4-alkyl; halo-C1-C4-alkoxy; C1-C4-alkylthio; halo-C1-C4-alkylthio; C1-C4-alkylsulfonyl; formyl; C1-C4-alkanoyl; hydroxy; halogen; cyano; nitro; amino; C1-C4-alkylamino; di-C1-C4-alkylamino; C2-C4-carboxyl; C1-C4-alkoxy-C2-C4-carbonyl; C2-C4-alkenyloxy-C2-C4-carbonyl; and C2-C4-alkynyloxy-C2-C4-carbonyl; and n is an integer from 0 to 3;
z is C3-C4 alkynyloxy;
Y is R4; R4 is CH$_3$;
X is H, a protecting group, or a group of the formula (III)

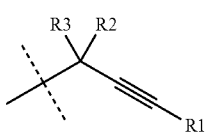

wherein R1, R2, and R3 are hydrogen.
11. A process for the preparation of a compound of formula (II)

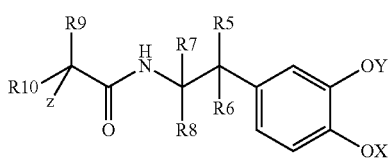

wherein
R5, R6, R7 and R8 are H;
R9 is H;
R10 is a group of the formula (VI)

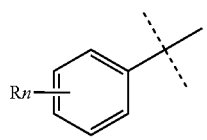

wherein R is halogen, C1-C4-alkyl, C2-C4-alkenyl, C2-C4-alkynyl, C3-C6-cycloalkyl, C3-C6-cycloalkyl-C1-C4-alkyl, phenyl or phenyl-C1-C4-alkyl, it being possible for any of the preceding groups (other than halogen) to be substituted by one or more identical or different groups selected from: C1-C4-alkoxy; C2-C4-alkenyloxy; C2-C4-alkynyloxy; C1-C4-alkoxy-C1-C4-alkyl; halo-C1-C4-alkoxy; C1-C4-alkylthio; halo-C1-C4-alkylthio; C1-C4-alkysulfonyl; formyl; C1-C4-alkanoyl; hydroxy; halogen; cyano; nitro; amino; C1-C4-alkylamino; di-C1-C4-alkylamino; C2-C4-carboxyl; C1-C4-alkoxy-C2-C4-carbonyl; C2-C4-alkenyloxy-C2-C4-carbonyl; and C2-C4-alkynyloxy-C2-C4-carbonyl; and n is an integer from 0 to 3;

z is C3-C4-alkynyloxy;

Y is R4; R4 is CH$_3$;

X is H, a protecting group, or a group of the formula (III)

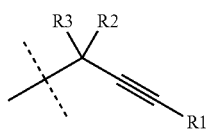

(III)

wherein R1, R2, and R3 are hydrogen;

comprising reacting a carboxylic acid of formula (IV)

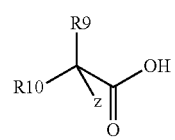

(IV)

with an amine of formula (V)

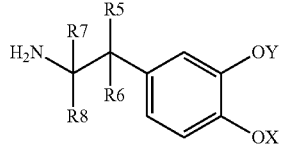

(V)

wherein the reaction is conducted in the absence of a catalyst.

12. The process according to claim 1, comprising the further steps of converting the compound of formula (II) to a fungicidally active compound of formula (I)

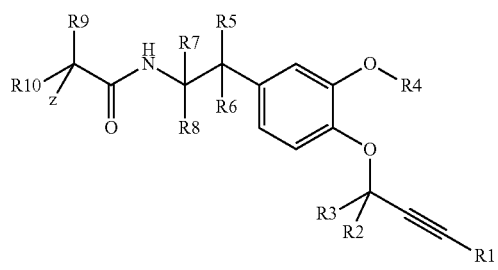

(I)

wherein R1 to R10 and Z are as defined in claim 1.

13. The process according to claim 1, comprising the further step of reacting the compound of formula (II) with a compound of formula (XII)

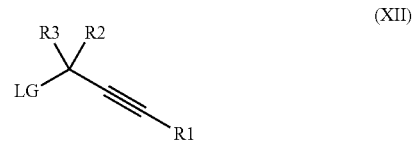

(XII)

wherein R1, R2 and R3 are as defined in claim 1 and LG is a leaving group, to give a compound of formula (I)

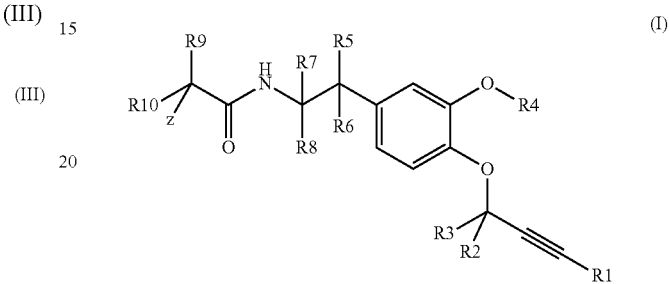

(I)

wherein R1 to R10 and Z are as defined in claim 1.

14. The process according to claim 1, for the preparation of a compound of formula (XIII)

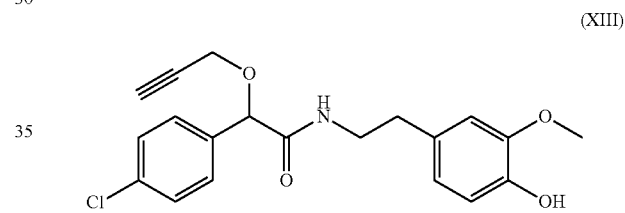

(XIII)

comprising reacting an acid of the formula (XIV)

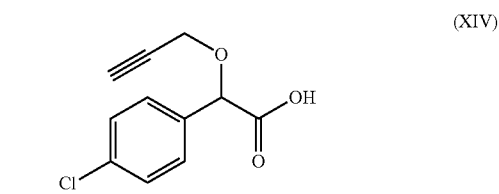

(XIV)

with an amine of the formula (XV)

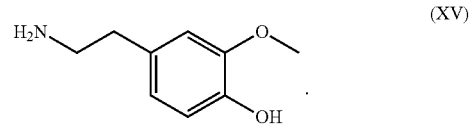

(XV)

15. A process according to claim 14, comprising the further step of reacting the compound of formula (XIII) with a compound of formula (XVII)

(XVII)

wherein LG is a leaving group to give mandipropamid (XVI)
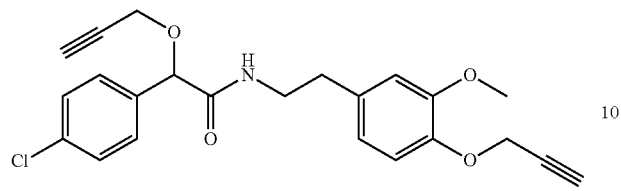
(XVI)
or an agriculturally acceptable salt thereof.
* * * * *